(12) United States Patent
Rossignol et al.

(10) Patent No.: US 10,358,428 B2
(45) Date of Patent: *Jul. 23, 2019

(54) COMPOSITIONS AND METHODS OF TREATMENT WITH PRODRUGS OF TIZOXANIDE, AN ANALOGUE OR SALT THEREOF

(71) Applicant: Romark Laboratories, L.C., Tampa, FL (US)

(72) Inventors: Jean-Francois Rossignol, St. Petersburg, FL (US); Andrew Stachulski, Tampa, FL (US)

(73) Assignee: Romark Laboratories, L.C., Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/153,070

(22) Filed: Oct. 5, 2018

(65) Prior Publication Data

US 2019/0040026 A1    Feb. 7, 2019

Related U.S. Application Data

(63) Continuation of application No. 15/525,658, filed as application No. PCT/US2015/060084 on Nov. 11, 2015, now Pat. No. 10,100,023.

(60) Provisional application No. 62/078,384, filed on Nov. 11, 2014.

(51) Int. Cl.

| | |
|---|---|
| C07D 277/58 | (2006.01) |
| A61K 9/20 | (2006.01) |
| A61K 9/48 | (2006.01) |
| A61K 31/426 | (2006.01) |
| A61K 45/06 | (2006.01) |
| C07D 277/46 | (2006.01) |
| A61K 31/138 | (2006.01) |
| A61K 31/506 | (2006.01) |
| A61K 31/555 | (2006.01) |
| A61K 31/704 | (2006.01) |
| A61K 31/7068 | (2006.01) |
| A61P 31/04 | (2006.01) |
| A61P 35/00 | (2006.01) |
| A61P 31/12 | (2006.01) |

(52) U.S. Cl.
CPC ............. *C07D 277/58* (2013.01); *A61K 9/20* (2013.01); *A61K 9/48* (2013.01); *A61K 31/138* (2013.01); *A61K 31/426* (2013.01); *A61K 31/506* (2013.01); *A61K 31/555* (2013.01); *A61K 31/704* (2013.01); *A61K 31/7068* (2013.01); *A61K 45/06* (2013.01); *A61P 31/04* (2018.01); *A61P 31/12* (2018.01); *A61P 35/00* (2018.01); *C07D 277/46* (2013.01)

(58) Field of Classification Search
CPC .................................................. C07D 277/58
See application file for complete search history.

(56) References Cited

U.S. PATENT DOCUMENTS

| | | |
|---|---|---|
| 3,950,351 A | 4/1976 | Rossignol et al. |
| 5,387,598 A | 2/1995 | Rossignol |
| 5,856,348 A | 1/1999 | Rossignol |
| 5,859,038 A | 1/1999 | Rossignol |
| 5,886,013 A | 3/1999 | Rossignol |
| 5,935,591 A | 8/1999 | Rossignol et al. |
| 5,965,590 A | 10/1999 | Rossignol |
| 5,968,961 A | 10/1999 | Rossignol |
| 6,020,353 A | 2/2000 | Rossignol |
| 6,117,894 A | 9/2000 | Rossignol |
| 7,285,567 B2 | 10/2007 | Rossignol |
| 7,550,493 B2 | 6/2009 | Rossignol |
| 7,645,783 B2 | 1/2010 | Rossignol |
| 8,124,632 B2 | 2/2012 | Rossignol et al. |
| 8,524,278 B2 | 9/2013 | Rossignol et al. |
| 8,633,230 B2 | 1/2014 | Rossignol |
| 8,772,502 B2 | 7/2014 | Semple et al. |
| 8,846,727 B2 | 9/2014 | Rossignol et al. |
| 8,895,752 B2 | 11/2014 | Rossignol et al. |
| 9,023,877 B2 | 5/2015 | Rossignol et al. |
| 9,107,913 B2 | 8/2015 | Rossignol |
| 9,126,992 B2 | 9/2015 | Rossignol et al. |
| 9,345,690 B2 | 5/2016 | Rossignol et al. |
| 9,351,937 B2 | 5/2016 | Rossignol et al. |
| 10,100,023 B2 * | 10/2018 | Rossignol ............... A61P 31/04 |
| 2005/0171169 A1 | 8/2005 | Rossignol |
| 2006/0089396 A1 | 4/2006 | Rossignol |
| 2006/0194853 A1 | 8/2006 | Rossignol |
| 2007/0015803 A1 | 1/2007 | Rossignol |
| 2007/0167504 A1 | 7/2007 | Rossignol |
| 2008/0097106 A1 | 4/2008 | Rossignol |

(Continued)

FOREIGN PATENT DOCUMENTS

WO    WO 2015/000431 A1    1/2015

OTHER PUBLICATIONS

Clerici et al., "The anti-infective Nitazoxanide shows strong immunomodulating effects," The Journal of Immunology, 2011, 186:155.21.
Rossignol et al. "Thiazolides, a New Class of Anti-influenza Molecules Targeting Viral Hemagglutinin at the Post-translational Level," The Journal of Biological Chemistry, Oct. 23, 2009, 284(43):29798-29808.
Rossignol, Jean-Francois, "Nitazoxanide: A first-in-class broad-spectrum antiviral agent," Antiviral Research, 2014, 110:94-101.
Santoro et al., "Thiazolides: A New Class of Broad-Spectrum Antiviral Drugs Targeting Virus Maturation," Antiviral Research, 2007, 74:A31.
PubChem CID 56970678, National Center for Biotechnology Information, PubChem Compound Database; CID=56970678, https://pubchem.ncbi.nlm.nih.gov/compound/056970678 (accessed Feb. 7, 2018, create date May 28, 2012.

Primary Examiner — Laura L Stockton
(74) Attorney, Agent, or Firm — Foley & Lardner LLP

(57) ABSTRACT

Prodrugs of tizoxanide, an analog or salt thereof are disclosed. The prodrugs have an ester moiety comprising an amino acid moiety, and increase the bioavailability of the tizoxanide, an analog or salt thereof. Compositions and methods of treating an intracellular protozoan infection, a viral infection or a cancer are also disclosed.

11 Claims, No Drawings

(56) References Cited

U.S. PATENT DOCUMENTS

| | | |
|---|---|---|
| 2008/0096941 A1 | 8/2008 | Rossignol |
| 2009/0036467 A1 | 2/2009 | Rossignol et al. |
| 2010/0209505 A1 | 8/2010 | Rossignol et al. |
| 2010/0292274 A1 | 11/2010 | Rossignol et al. |
| 2010/0330173 A1 | 12/2010 | Rossignol et al. |
| 2012/0108592 A1 | 5/2012 | Semple et al. |
| 2012/0122939 A1 | 5/2012 | Rossignol et al. |
| 2012/0294831 A1 | 11/2012 | Rossignol |
| 2013/0317070 A1 | 11/2013 | Hoffman et al. |
| 2014/0112888 A1 | 4/2014 | Rossignol |
| 2014/0341850 A1 | 11/2014 | Rossignol et al. |
| 2015/0250768 A1 | 9/2015 | Rossignol et al. |
| 2016/0228415 A1 | 8/2016 | Rossignol et al. |
| 2016/0243087 A1 | 8/2016 | Rossignol et al. |
| 2016/0340326 A1 | 11/2016 | Li et al. |

\* cited by examiner

COMPOSITIONS AND METHODS OF TREATMENT WITH PRODRUGS OF TIZOXANIDE, AN ANALOGUE OR SALT THEREOF

This application is a Continuation of U.S. application Ser. No. 15/525,658, which is the U.S. National stage of PCT/US2015/060084, filed Nov. 11, 2015, which claims the benefit of U.S. Provisional Application Ser. No. 62/078,384, filed Nov. 11, 2014, which is incorporated by reference herein.

BACKGROUND

Nitazoxanide (2-(acetolyloxy)-N-(5-nitro-2-thiazolyl)benzamide) is a compound having the following structure:

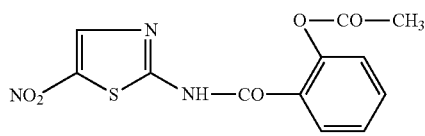 [SMILES: CC(=O)Oc1ccccc1C(=O)Nc1ncc([N+](=O)[O-])s1]

Tizoxanide is the active circulating metabolite of nitazoxanide.

The preparation and uses of nitazoxanide are disclosed, for example, in U.S. Pat. No. 3,950,351 to Rossignol.

Pharmaceutical compositions containing nitazoxanide and its metabolite, tizoxanide, were originally developed and marketed for treating intestinal parasitic infections. However, nitazoxanide, tizoxanide and various analogues thereof have been shown to have activity against various intracellular protozoan infections, viral infections, including influenza and hepatitis, and cancers. See U.S. Pat. Nos. 8,524,278, 8,124,632, 7,645,783, 7,550,493, 7,285,567, 6,117,894, 6,020,353, 5,968,961, 5,965,590, 5,935,591, and 5,886,013, and U.S. application Ser. Nos. 12/184,760, 12/656,704, 12/821,571, 12/777,383, 13/284,242, 13/471,948, which are herein incorporated by reference in their entirety.

Furthermore, nitazoxanide, tizoxanide and various analogues thereof are capable of stimulating an immune response in subjects, which can result in treatment or prevention of an intracellular protozoan infection, a viral infection or a cancer.

Following oral administration of nitazoxanide or mixtures of nitazoxanide plus tizoxanide in humans, these compounds are partially absorbed from the intestinal tract, and nitazoxanide is rapidly hydrolyzed to form tizoxanide in plasma. Tizoxanide is glucurono-conjugated, and the drug is eliminated in urine and bile as tizoxanide or tizoxanide glucuronide. The half-life of tizoxanide in plasma is only approximately 1.5 hours.

Given this short half-life, and the relatively low bioavailability of nitazoxanide, tizoxanide and various analogues thereof there remains a need for compounds having a similar activity to nitazoxanide, tizoxanide and various analogues thereof, but with greater bioavailability.

SUMMARY OF THE DISCLOSED SUBJECT MATTER

One embodiment of the invention relates to a compound represented by:

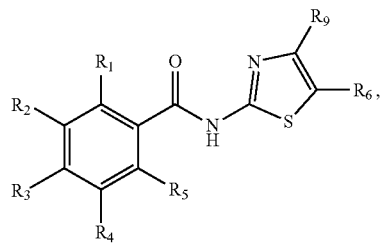

wherein $R_1$ through $R_5$ are, independently, selected from the group consisting of hydrogen, CN, $NO_2$, F, Cl, Br, I, hydroxy, alkyl, alkenyl, alkynyl, cycloalkyl, cycloalkylalkyl, cycloalkylalkenyl, cycloalkylalkynyl, cycloalkenyl, cycloalkenylalkyl, cycloalkenylalkenyl, cycloalkenylalkynyl, alkoxy, alkenyloxy, alkynyloxy, alkoxyalkyl, alkoxyalkenyl, alkoxyalkynyl, alkenyloxyalkyl, alkenyloxyalkenyl, alkenyloxyalkynyl, alkynyloxyalkyl, alkenyloxyalkenyl, alkenyloxyalkynyl, cycloalkoxy, cycloalkylalkoxy, cycloalkylalkenyloxy, cycloalkylalkynyloxy, cycloalkenyloxy, cycloalkenylalkoxy, cycloalkenylalkenyloxy, cycloalkenylalkynyloxy, alkoxyalkylamino, hydroxyalkyl, acyl, acyloxy, aroyloxy, arylalkanoyloxy, arylalkenoyloxy, heteroaroyloxy, heteroarylalkanoyloxy, heteroarylalkenoyloxy, alkoxycarbonyl, aryloxycarbonyl, arylalkoxycarbonyl, heteroaryloxycarbonyl, heteroarylalkoxycarbonyl, alkoxycarbonyloxy, carbamoyl, carbamoyloxy, alkylamino, dialkylamino, alkylaminoalkyl, amido, alkylamido, dialkylamido, haloalkyl, perhaloalkyl, perhaloalkoxy, alkylthio, alkylthioalkyl, alkylsulfonyl, alkylsulfonylalkyl, alkenylsulfonyl, alkynylsulfonyl, cycloalkylsulfonyl, cycloalkylalkylsulfonyl, cycloalkylsulfonylalkyl, cycloalkylalkylsulfonylalkyl, arylsulfonyl, arylalkylsulfonyl, arylalkenylsulfonyl, heteroarylsulfonyl, heteroarylalkylsulfonyl, heteroarylalkenylsulfonyl, alkylsulfonamido, N,N'-dialkylsulfonamido, sulfonamidoalkyl, sulfonamidoaryl, sulfonamidoarylalkyl, sulfonamidoarylalkenyl, aryl, arylalkyl, aryloxy, arylalkoxy, arylthio, arylalkylthio, arylamino, arylalkylamino, arylalkenyl, arylalkynyl, heteroaryl, heteroarylalkyl, heteroarylalkenyl, heteroarylalkynyl, heteroaryloxy, heteroarylalkoxy, heteroarylamino, heteroarylalkylamino, heteroarylthio, heteroarylalkylthio, heteroarylalkylamino, heterocycloalkyl, heterocycloalkenyl, heterocycloalkoxy, and heterocycloalkenyloxy, any of which may be optionally substituted;

and where each of $R_1$ through $R_5$ comprises 1 to 60 atoms;

provided at least one of $R_1$ through $R_5$ is an amino acid is selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine, or a moiety represented by Formula A:

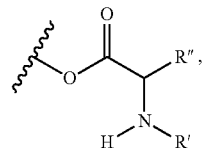

wherein R' is selected from the group consisting of hydrogen, alkyl, and a nitrogen protecting group;

R" is selected from the group consisting of alkyl, alkenyl, alkynyl, cycloalkyl, cycloalkylalkyl, cycloalkylalkenyl, cycloalkylalkynyl, cycloalkenyl, cycloalkenylalkyl, cycloalkenylalkenyl, cycloalkenylalkynyl;

one of $R_6$ and $R_9$ is selected from the group consisting of $NO_2$, F, Cl, Br, $-SO_2-(C_1-C_{10})$-alkyl, $-SO-(C_1-C_{10})$-alkyl, haloalkyl, perhaloalkyl, haloalkoxy, perhaloalkoxy, $S(O)_mC(R_7R_8)_nCF_3$, and $C(R_2R_8)_nCF_3$; and the other of $R_6$ and $R_9$ that is not selected from the group, is hydrogen;

or a pharmaceutically acceptable salt thereof.

In another embodiment, $R_6$ is selected from the group consisting of $NO_2$, F, Cl, Br, $-SO_2-(C_1-C_{10})$-alkyl, $-SO-(C_1-C_{10})$-alkyl, haloalkyl, perhaloalkyl, haloalkoxy, perhaloalkoxy, $S(O)_mC(R_7R_8)_nCF_3$, and $C(R_7R_8)_nCF_3$, and $R_9$ is hydrogen, or wherein $R_9$ is selected from the group consisting of $NO_2$, F, Cl, Br, $-SO_2-(C_1-C_{10})$-alkyl, $-SO-(C_1-C_{10})$-alkyl, haloalkyl, perhaloalkyl, haloalkoxy, perhaloalkoxy, $S(O)_mC(R_2R_8)_nCF_3$, and $C(R_7R_8)_nCF_3$, and $R_6$ is hydrogen. In another embodiment, $R_6$ is selected from the group consisting of $NO_2$, F, Cl, Br, $-SO_2-(C_1-C_{10})$-alkyl, and $-SO-(C_1-C_{10})$-alkyl, and $R_9$ is hydrogen, or wherein $R_9$ is selected from the group consisting of $NO_2$, F, Cl, Br, $-SO_2-(C_1-C_{10})$-alkyl, and $-SO-(C_1-C_{10})$-alkyl, and $R_6$ is hydrogen. In another embodiment, $R_6$ is selected from the group consisting of $NO_2$ and Cl, and $R_9$ is hydrogen, or wherein $R_9$ is selected from the group consisting of $NO_2$ and Cl, and $R_6$ is hydrogen. In another embodiment, $R_9$ is hydrogen. In another embodiment, $R_6$ is hydrogen.

In another embodiment, R' is selected from the group consisting of hydrogen and a nitrogen protecting group, and R" is a straight-chain, branched-chain, or cyclic unsaturated $(C_1-C_{10})$-alkyl moiety.

In another embodiment, R" is a straight-chain or branched-chain $(C_1-C_5)$-alkyl moiety. In another embodiment, R" is a $(C_1-C_4)$-alkyl moiety. In another embodiment, R" is a $C_{3-4}$-alkyl moiety, or a t-Bu moiety. In another embodiment, R' is hydrogen.

In another embodiment, Formula A is a moiety selected from

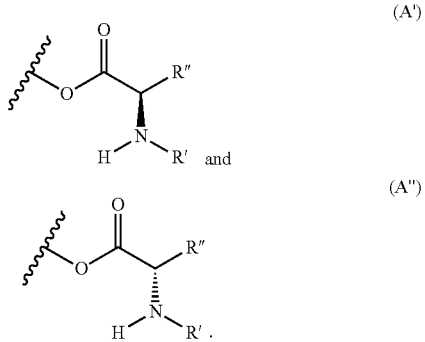

In another embodiment, one of $R_1$ through $R_3$ is a moiety represented by Formula A, and the remaining of $R_1$ through $R_5$ are hydrogen.

In another embodiment, $R_1$ is a moiety represented by Formula A, and $R_2$ through $R_5$ are hydrogen.

In another embodiment, $R_2$ is a moiety represented by Formula A, and $R_1$ and $R_3$ through $R_5$ are hydrogen.

In another embodiment, $R_3$ is a moiety represented by Formula A, and $R_1$, $R_2$, $R_4$ and $R_5$ are hydrogen.

Another embodiment of the invention relates to a pharmaceutical composition comprising a compound, or pharmaceutically acceptable salt thereof, of any of the preceding embodiments, and a pharmaceutically acceptable excipient.

In another embodiment, the pharmaceutical composition is in the form of a solid oral dosage form.

In another embodiment, the solid oral dosage form is a tablet.

In another embodiment, the solid oral dosage form is a capsule.

Another embodiment of the invention relates to a pharmaceutical composition of any of the preceding composition embodiments, wherein the pharmaceutical composition is in the form of a solid oral dosage form comprising:

(a) a first portion comprising a first quantity of any of the above compounds, or a pharmaceutically acceptable salt thereof, in a controlled release formulation; and (b) a second portion comprising a second quantity of any of the above compounds, or a pharmaceutically acceptable salt thereof, in an immediate release formulation.

Another embodiment of the invention relates to a pharmaceutical composition of any of the preceding composition embodiments, wherein the pharmaceutical composition is in the form of a solid oral dosage form comprising a quantity of a compound of any of the preceding embodiments or a pharmaceutically acceptable salt thereof, in a controlled release formulation.

A pharmaceutical composition of any of the preceding composition embodiments, wherein the pharmaceutical composition comprises one or more diluents, disintegrants, binders, suspending agents, glidants, lubricants, or fillers.

A pharmaceutical composition of any of the preceding composition embodiments, wherein, when the pharmaceutical composition comprises a controlled release formulation.

A pharmaceutical composition of any of the preceding compositions so that when ingested orally, the composition induces statistically significant higher bioavailability of a derivative of the compound of any of the preceding embodiments or the pharmaceutically acceptable salt thereof.

The pharmaceutical composition of the preceding embodiments, wherein the derivative of the compound of any of the preceding embodiments is a derivative that does not include the moiety represented by Formula A.

Another embodiment of the invention relates to a method of treating an intracellular protozoan infection, a viral infection or a cancer, comprising administering to a patient in need thereof a therapeutically effective amount of a compound or composition of any of the preceding claims.

In another embodiment, the compound of any of the compound embodiments is administered in combination with at least one additional component selected from the group consisting of a vaccine, an immunostimulant, a neuraminidase inhibitor, an adamantine analogue, and a recombinant sialidase fusion protein.

In another embodiment, the method is a method of treating a viral infection in a patient in need thereof.

In another embodiment, the viral infection is influenza infection.

In another embodiment, the viral infection is caused by a virus selected from H1N1, H2N2, H3N2, H5N1, H7N7, H1N2, H9N2, H7N2, H7N3, and H10N7.

In another embodiment, the viral infection is Hepatitis B.

In another embodiment, the method is a method of treating a cancer in a patient in need thereof.

In another embodiment, the cancer is leukemia.

In another embodiment, the leukemia is hairy cell leukemia or chronic myeloid leukemia.

In another embodiment, the cancer is melanoma.

In another embodiment, the cancer is non-Hodgkin lymphoma.

In another embodiment, the cancer is renal cell carcinoma.

In another embodiment, the compound of composition is administered in combination with at least one of a vaccine, an immunostimulant and an anticancer drug.

In another embodiment, the compound of composition is administered in combination with at least one anticancer drug is selected from the group consisting of STI571, CGP 74588, 1-β-D-Arabinofuranosylcytosine (Ara-C), doxorbicin, dacarbazine, cisplatin, bleomycin, vincristine, lomustine, vinblastine, carmustine, DTIC, tamoxifen, sunitinib, sorafenib and interferon-α.

In another embodiment, the method is a method of treating an intracellular protozoan infection in a patient in need thereof.

A method of increasing the bioavailability of a thiazolide compound comprising administering a compound, or salt thereof, of any of proceeding compound embodiments, to a mammal, wherein the bioavailability is increased in relation to administration of nitazoxanide.

DETAILED DESCRIPTION

Introduction

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about". The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

By "pharmaceutically acceptable" is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. and Drug administration.

By "patient" is meant any animal for which treatment is desirable. Patients may be mammals, and typically, as used herein, a patient is a human individual.

The term "pharmaceutically acceptable salt," as used herein, represents salts or zwitterionic forms of the compounds of the present invention which are water or oil-soluble or dispersible; which are suitable for treatment of diseases without undue toxicity, irritation, and allergic-response; which are commensurate with a reasonable benefit/risk ratio; and which are effective for their intended use. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form pharmaceutically acceptable addition salts include inorganic acids such as hydrochloric, hydrobromic, sulfuric, and phosphoric, and organic acids such as oxalic, malcic, succinic, and citric. Salts can also be formed by coordination of the compounds with an alkali metal or alkaline earth ion. Hence, the present invention contemplates sodium, potassium, magnesium, and calcium salts of the compounds of the compounds of the present invention and the like.

The term "solvates" is used in its broadest sense. For example, the term solvates includes hydrates formed when a compound of the present invention contains one or more bound water molecules.

The term "alkyl," as used herein, alone or in combination, refers to a straight-chain or branched-chain alkyl radical containing from 1 to and including 20, preferably 1 to 10, and more preferably 1 to 6, carbon atoms. The term "alkyl groups" is used in its broadest sense. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. For example, the $O(C_1-C_8)$-alkyl groups comprises the straight $O(C_1-C_8)$-alkyl groups as well as the branched $O(C_1-C_8)$-alkyl groups. For another example, the term comprises cycloalkyl groups, as for example, the $(C_1-C_8)$-alkyl groups comprises the $(C_3-C_8)$-cycloalkyl groups.

The term "alkenyl" is used in its broadest sense. For example, the term alkenyl refers to branched, unbranched, and cyclic unsaturated hydrocarbon chains comprising a designated number of carbon atoms. For example, $(C_2-C_8)$ alkenyl embraces straight, branched, and cyclic hydrocarbon chains containing 2 to 8 carbon atoms having at least one double bond, and the term includes but is not limited to substituents such as ethenyl, propenyl, iso-propenyl, butenyl, iso-butenyl, sec-butenyl, tert-butenyl, n-pentenyl, n-hexenyl, and the like, unless otherwise indicated.

The term "alkynyl" is used in its broadest sense. For example, the term alkynyl refers to branched, unbranched, and cyclic unsaturated hydrocarbon chains comprising a designated number of carbon atoms. For example, $(C_2-C_8)$ alkynyl embraces straight, branched, and cyclic hydrocarbon chains containing 2 to 8 carbon atoms having at least one triple bond, and the term includes but is not limited to substituents such as ethynyl, propynyl, butenyl, n-pentynyl and branched counterparts, n-hexynyl and branched counterparts, and the like, unless otherwise indicated.

The term "cycloalkyl," as used herein, alone or in combination, refers to a saturated or partially saturated monocyclic, bicyclic or tricyclic alkyl radical wherein each cyclic moiety contains from 3 to 12, preferably three to seven, carbon atom ring members and which may optionally be a benzo fused ring system which is optionally substituted as defined herein. Examples of such cycloalkyl radicals include cyclopropyl, cyclobutyl, cyclopentyl, cyclohexyl, cycloheptyl, octahydronaphthyl, 2,3-dihydro-1H-indenyl, adamantyl and the like. "Bicyclic" and "tricyclic" as used herein are intended to include both fused ring systems, such as decahydonapthalene, octahydronapthalene as well as the multicyclic (multicentered) saturated or partially unsaturated type. The latter type of isomer is exemplified in general by bicyclo[2,2,2]octane, bicyclo[2,2,2]octane, bicyclo[1,1,1] pentane, camphor and bicyclo[3,2,1]octane.

The term "cycloalkenyl," as used herein, alone or in combination, refers to a partially unsaturated monocyclic, bicyclic or tricyclic radical wherein each cyclic moiety contains from 3 to 12, preferably five to eight, carbon atom ring members and which may optionally be a benzo fused ring system which is optionally substituted as defined herein. Examples of such cycloalkenyl radicals include cyclopentenyl, cyclohexenyl, cyclohexadienyl, cycloheptenyl, cyclooctadienyl, -1H-indenyl and the like.

The term "cycloalkylalkyl," as used herein, alone or in combination, refers to an alkyl radical as defined above which is substituted by a cycloalkyl radical as defined above. Examples of such cycloalkylalkyl radicals include cyclopropylmethyl, cyclobutylmethyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, cyclohexylbutyl and the like.

The term "cycloalkenylalkyl," as used herein, alone or in combination, refers to an alkyl radical as defined above which is substituted by a cycloalkenyl radical as defined above. Examples of such cycloalkenylalkyl radicals include 1-methylcyclohex-1-enyl-, 4-ethylcyclohex-1-enyl-, 1-butylcyclopent-1-enyl-, 3-methylcyclopent-1-enyl- and the like.

The term "ester," as used herein, alone or in combination, refers to a carbonyloxy —(C=O)O— group bridging two moieties linked at carbon atoms. Examples include ethyl benzoate, n-butyl cinnamate, phenyl acetate and the like.

The term "acyl," as used herein, alone or in combination, refers to a carbonyl attached to an alkyl, alkenyl, aryl, heteroaryl, heterocycle, or any other moiety where the atom attached to the carbonyl is carbon. An "acetyl" group refers to a —C(O)CH$_3$ group. Examples of acyl groups include alkanoyl groups such as formyl, acetyl, and propionyl, aroyl groups such as benzoyl, and mixed alkyl-aryl groups such as cinnamoyl.

The term "alkoxycarbonyl," as used herein, alone or in combination, refers to an alkoxy group attached to the parent molecular moiety through a carbonyl group. Examples of such "alkoxycarbonyl" groups include methoxycarbonyl, ethoxycarbonyl, propoxycarbonyl, butoxycarbonyl and hexyloxycarbonyl.

The term "alkylamino," as used herein, alone or in combination, refers to an amino group attached to the parent molecular moiety through an alkyl group.

The term "alkanoyl," as used herein, refers to an alkyl group attached to the parent molecular moiety through a carbonyl group. Examples of such groups include methylcarbonyl, also known as acetyl; ethylcarbonyl, also known as propionyl; and 2-methyl-cyclopentylcarbonyl, etc.

The term "alkylsulfonyl," as used herein, alone or in combination, refers to an alkyl group attached to the parent molecular moiety through a sulfonyl group. Examples of alkylsulfinyl groups include methanesulfonyl, ethanesulfonyl, tert-butanesulfonyl, and the like.

The term "alkylthio," as used herein, alone or in combination, refers to an alkyl thioether (R—S—) radical wherein the term alkyl is as defined above. Examples of suitable alkyl thioether radicals include methylthio, ethylthio, n-propylthio, isopropylthio, n-butylthio, iso-butylthio, sec-butylthio, tert-butylthio, ethoxyethylthio, methoxypropoxyethylthio, ethoxypentoxyethylthio and the like.

The term "alkylthioalkyl" embraces alkylthio radicals attached to an alkyl radical. Alkylthioalkyl radicals include "lower alkylthioalkyl" radicals having alkyl radicals of one to six carbon atoms and an alkylthio radical as described above. Examples of such radicals include methylthiomethyl.

The term "amido," as used herein, alone or in combination, refers to an amino group as described below attached to the parent molecular moiety through a carbonyl or sulfonyl group. The term "C-amido" as used herein, alone or in combination, refers to a —C(=O)—NR$_2$ group with R as defined herein. The term "N-amido" as used herein, alone or in combination, refers to a RC(=O)NH— group, with R as defined herein.

The term "amino," as used herein, alone or in combination, refers to —NRR', wherein R and R' are independently selected from the group consisting of hydrogen, alkenyl, alkoxy, alkoxyalkyl, alkoxycarbonyl, alkyl, alkylcarbonyl, aryl, arylalkenyl, arylalkyl, cycloalkyl, haloalkylcarbonyl, heteroaryl, heteroarylalkenyl, heteroarylalkyl, heterocycle, heterocycloalkenyl, and heterocycloalkyl, wherein the aryl, the aryl part of the arylalkenyl, the arylalkyl, the heteroaryl, the heteroaryl part of the heteroarylalkenyl and the heteroarylalkyl, the heterocycle, and the heterocycle part of the heterocycloalkenyl and the heterocycloalkyl can be optionally substituted with one, two, three, four, or five substituents independently selected from the group consisting of alkenyl, alkoxy, alkoxyalkyl, alkyl, cyano, halo, haloalkoxy, haloalkyl, hydroxy, hydroxy-alkyl, nitro, and oxo.

The term "aminoalkyl," as used herein, alone or in combination, refers to an amino group attached to the parent molecular moiety through an alkyl group. Examples include aminomethyl, aminoethyl and aminobutyl. The term "alkylamino" denotes amino groups which have been substituted with one or two alkyl radicals. Suitable "alkylamino" groups may be mono- or dialkylated, forming groups such as, for example, N-methylamino, N-ethylamino, N,N-dimethylamino, N,N-diethylamino and the like.

The terms "aminocarbonyl" and "carbamoyl," as used herein, alone or in combination, refer to an amino-substituted carbonyl group, wherein the amino group can be a primary or secondary amino group containing substituents selected from alkyl, aryl, aralkyl, cycloalkyl, cycloalkylalkyl radicals and the like.

The term "aryl," as used herein, alone or in combination, means a carbocyclic aromatic system containing one, two or three rings wherein such rings may be attached together in a pendent manner or may be fused. The term "aryl" embraces aromatic radicals such as phenyl, naphthyl, anthracenyl, phenanthryl, and biphenyl. The aryl groups of the present invention can be optionally substituted with one, two, three, four, or five substituents independently selected from the groups as defined herein.

The term "arylalkenyl," as used herein, refers to an aryl group attached to the parent molecular moiety through an alkenyl group.

The term "arylalkoxy," as used herein, refers to an aryl group attached to the parent molecular moiety through an alkoxy group.

The term "arylamino" as used herein, alone or in combination, refers to an aryl group attached to the parent moiety through an amino group, such as N-phenylamino, and the like.

The term "aryloxy," as used herein, alone or in combination, refers to an aryl group attached to the parent molecular moiety through an oxygen atom.

The term "arylsulfonyl," as used herein, alone or in combination, refers to an aryl group attached to the parent molecular moiety through a sulfonyl group.

The term "arylthio," as used herein, alone or in combination, refers to an aryl group attached to the parent molecular moiety through a sulfur atom.

The terms "carboxy" or "carboxyl," whether used alone or with other terms, such as "carboxyalkyl," denotes —CO$_2$H.

The terms "benzo" and "benz," as used herein, alone or in combination, refer to the divalent radical C$_6$H$_4$= derived from benzene. Examples include benzothiophene and benzimidazole.

The term "carbamoyloxy," as used herein, alone or in combination, refers to an amino-substituted carbonyl group attached to the parent molecular moiety through an oxygen atom (e.g. RR'NC(=O)O—), wherein the amino group can be a primary or secondary amino group containing substituents selected from alkyl, aryl, aralkyl, cycloalkyl, cycloalkylalkyl radicals and the like.

The term "carbonate" as used herein, alone or in combination, refers to a —O—C(=O)OR group, with R as defined herein.

The term "carbonyl," as used herein, when alone includes formyl [—C(O)H] and in combination is a —C(O)— group.

The term "carboxy," as used herein, refers to —C(O)OH or the corresponding "carboxylate" such as a carboxylic acid salt derivative or ester derivative. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," as used herein, alone or in combination, refers to a saturated or partially saturated monocyclic, bicyclic or tricyclic alkyl radical wherein each cyclic moiety contains from 3 to 12, preferably three to seven, carbon atom ring members and which may optionally be a benzo fused ring system which is optionally substituted as defined herein. Examples of such cycloalkyl radicals include cyclopropyl, cyclobutyl, cyclopentyl, cyclohexyl, cycloheptyl, octahydronaphthyl, 2,3-dihydro-1H-indenyl, adamantyl and the like. "Bicyclic" and "tricyclic" as used herein are intended to include both fused ring systems, such as decahydonapthalene, octahydronapthalene as well as the multicyclic (multicentered) saturated or partially unsaturated type. The latter type of isomer is exemplified in general by bicyclo[2,2,2]octane, bicyclo[2,2,2]octane, bicyclo[1,1,1]pentane, camphor and bicyclo[3,2,1]octane.

The term "cycloalkenyl," as used herein, alone or in combination, refers to a partially unsaturated monocyclic, bicyclic or tricyclic radical wherein each cyclic moiety contains from 3 to 12, preferably five to eight, carbon atom ring members and which may optionally be a benzo fused ring system which is optionally substituted as defined herein. Examples of such cycloalkenyl radicals include cyclopentenyl, cyclohexenyl, cyclohexadienyl, cycloheptenyl, cyclooctadienyl, -1H-indenyl and the like.

The term "cycloalkylalkyl," as used herein, alone or in combination, refers to an alkyl radical as defined above which is substituted by a cycloalkyl radical as defined above. Examples of such cycloalkylalkyl radicals include cyclopropylmethyl, cyclobutylmethyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, cyclohexylbutyl and the like.

The term "cycloalkenylalkyl," as used herein, alone or in combination, refers to an alkyl radical as defined above which is substituted by a cycloalkenyl radical as defined above. Examples of such cycloalkenylalkyl radicals include 1-methylcyclohex-1-enyl-, 4-ethylcyclohex-1-enyl-, 1-butylcyclopent-1-enyl-, 3-methylcyclopent-1-enyl- and the like.

The term "ester," as used herein, alone or in combination, refers to a carbonyloxy —(C=O)O— group bridging two moieties linked at carbon atoms. Examples include ethyl benzoate, n-butyl cinnamate, phenyl acetate and the like.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, trichloroethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a halohydrocarbyl group attached at two or more positions. Examples include fluoromethylene (—CFH—), difluoromethylene (—CF$_2$—), chloromethylene (—CHCl—) and the like. Examples of such haloalkyl radicals include chloromethyl, 1-bromoethyl, fluoromethyl, difluoromethyl, trifluoromethyl, 1,1,1-trifluoroethyl, perfluorodecyl and the like.

The term "heteroalkyl," as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH$_2$—NH—OCH$_3$.

The term "heteroaryl," as used herein, alone or in combination, refers to an aromatic five- or six-membered ring, where at least one atom is selected from the group consisting of N, O, and S, and the remaining ring atoms are carbon. The five-membered rings have two double bonds, and the six-membered rings have three double bonds. The heteroaryl groups are connected to the parent molecular group through a substitutable carbon or nitrogen atom in the ring. The term "heteroaryl" also includes systems where a heteroaryl ring is fused to an aryl group, as defined herein, a heterocycle group, as defined herein, or an additional heteroaryl group. Heteroaryls are exemplified by benzothienyl, benzoxazolyl, benzofuranyl, benzimidazolyl, benzthiazolyl benzotriazolyl, cinnolinyl, furyl, imidazolyl, triazolyl [e.g., 4H-1,2,4-triazolyl, 1H-1,2,3-triazolyl, 2H-1,2,3-triazolyl, etc.], tetrazolyl [e.g. 1H-tetrazolyl, 2H-tetrazolyl, etc.], indazolyl, indolyl, isoxazolyl, isoquinolinyl, isothiazolyl, naphthyridinyl, oxadiazolyl [e.g., 1,2,4-oxadiazolyl, 1,3,4-oxadiazolyl, 1,2,5-oxadiazolyl, etc.], oxazolyl, isoxazolyl, purinyl, thiazolyl, isothiazolyl, thienopyridinyl, thienyl, thiadiazolyl [e.g., 1,2,4-thiadiazolyl, 1,3,4-thiadiazolyl, 1,2,5-thiadiazolyl, etc.], pyridinyl, pyridazinyl, pyrimidinyl, pyrazinyl, pyrazolyl, pyrrolyl, pyrido[2,3-d]pyrimidinyl, pyrrolo[2,3-b]pyridinyl, quinazolinyl, quinolinyl, thieno[2,3-c]pyridinyl, tetrazolyl, triazinyl, and the like. The heteroaryl groups of the present invention can be optionally substituted with one, two, three, four, or five substituents independently selected from the groups as defined herein.

Examples of heteroaryl groups include, without limitation, thienyl, benzothienyl, furyl, benzofuryl, dibenzofuryl, pyrrolyl, imidazolyl, pyrazolyl, pyridyl, pyrazinyl, pyrimidinyl, indolyl, quinolyl, isoquinolyl, quinoxalinyl, tetrazolyl, oxazolyl, thiazolyl, triazolyl, and isoxazolyl The term "heteroaralkyl" or "heteroarylalkyl," as used herein, alone or in combination, refers to a heteroaryl group attached to the parent molecular moiety through an alkyl group.

The term "heteroaralkenyl" or "heteroarylalkenyl," as used herein, alone or in combination, refers to a heteroaryl group attached to the parent molecular moiety through an alkenyl group.

The term "heteroaralkoxy" or "heteroarylalkoxy," as used herein, alone or in combination, refers to a heteroaryl group attached to the parent molecular moiety through an alkoxy group.

The term "heteroaralkylidene" or "heteroarylalkylidene," as used herein, alone or in combination, refers to a heteroaryl group attached to the parent molecular moiety through an alkylidene group.

The term "heteroaryloxy," as used herein, alone or in combination, refers to a heteroaryl group attached to the parent molecular moiety through an oxygen atom.

The term "heteroarylsulfonyl," as used herein, alone or in combination, refers to a heteroaryl group attached to the parent molecular moiety through a sulfonyl group.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic radical containing one or more heteroatoms as ring members, wherein each said heteroatom may be independently selected from the group consisting of nitrogen, oxygen, and sulfur, and wherein there are typically 3 to 8 ring members in each ring. Most commonly heterocyclic rings contain 5 to 6 ring members. In some embodiments of this invention heterocyclic rings contain 1 to 4 heteroatoms; in other embodiments, heterocyclic rings contain 1 to 2 heteroatoms. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Heterocycle groups of the invention are exemplified by aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "heterocycloalkenyl," as used herein, alone or in combination, refers to a heterocycle group attached to the parent molecular moiety through an alkenyl group.

The term "heterocycloalkoxy," as used herein, alone or in combination, refers to a heterocycle group attached to the parent molecular group through an oxygen atom.

The term "heterocycloalkylalkyl," as used herein, alone or in combination, refers to an alkyl radical as defined above in which at least one hydrogen atom is replaced by a heterocycloalkyl radical as defined above, such as pyrrolidinylmethyl, tetrahydrothienylmethyl, pyridylmethyl and the like.

The term "heterocycloalkylidene," as used herein, alone or in combination, refers to a heterocycle group attached to the parent molecular moiety through an alkylidene group.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl" as used herein, alone or in combination, refers to a linear or branched alkyl group having one to about ten carbon atoms any one of which may be substituted with one or more hydroxyl radicals. Examples of such radicals include hydroxymethyl, hydroxyethyl, hydroxypropyl, hydroxybutyl and hydroxyhexyl.

The term "hydroxyalkyl," as used herein, alone or in combination, refers to a hydroxy group attached to the parent molecular moiety through an alkyl group.

The term "lower," as used herein in such terms as "lower alkyl," alone or in combination, means containing from 1 to and including 6 carbon atoms.

The term "optionally substituted" means the anteceding group may be substituted or unsubstituted. When substituted, the hydrogen atoms bound to the carbon, nitrogen, sulfur, or oxygen atoms are replaced by "substituents" which may include carbonyl (oxo), carboxyl, lower alkyl carboxylate, lower alkyl carbonate, lower alkyl carbamate, halogen, hydroxy, amino, amido, cyano, hydrazinyl, hydrazinylcarbonyl, alkylhydrazinyl, dialkylhydrazinyl, aiylhydrazinyl, heteroarylhydrazinyl, nitro, thiol, sulfonic acid, trisubstituted silyl, urea, acyl, acyloxy, acylamino, acylthio, lower alkyl, lower alkylamino, lower dialkylamino, lower alkyloxy, lower alkoxyalkyl, lower alkylthio, lower alkylsulfonyl, lower alkenyl, lower alkenylamino, lower dialkenylamino, lower alkenyloxy, lower alkenylthio, lower alkenyl sulfonyl, lower alkynyl, lower alkynylamino, lower dialkynylamino, lower alkynyloxy, lower alkynylthio, lower alkynylsulfonyl, lower cycloalkyl, lower cycloalkyloxy, lower cycloalkylamino, lower cycloalkylthio, lower cycloalkylsulfonyl, lower cycloalkylalkyl, lower cycloalkylalkyloxy, lower cycloalkylalkylamino, lower cycloalkylalkylthio, lower cycloalkylalkylsulfonyl, aryl, aryloxy, arylamino, arylthio, arylsulfonyl, arylalkyl, arylalkyloxy, arylalkylamino, arylalkylthio, arylalkylsulfonyl, heteroaryl, heteroaryloxy, heteroarylamino, heteroarylthio, heteroarylsulfonyl, heteroarylalkyl, heteroarylalkyloxy, heteroarylalkylamino, heteroarylalkylthio, heteroarylalkylsulfonyl, heterocycloalkyl, heterocycloalkyloxy, heterocycloalkylamino, heterocycloalkylthio, heterocycloalkylsulfonyl, lower haloalkyl, lower haloalkenyl, lower haloalkynyl, lower perhaloalkyl, lower perhaloalkoxy, lower haloalkoxy, and lower acyloxy. Two substituents may be joined together to form a fused four-, five-, six-, or seven-membered carbocyclic or heterocyclic ring consisting of zero to three heteroatoms, for example forming methylenedioxy or ethylenedioxy. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. All pendant aryl, heteroaryl, and heterocyclo moieties can be further optionally substituted with one, two, three, four, or five substituents independently selected from the groups listed above.

The terms "oxy" or "oxa," as used herein, alone or in combination, refer to —O—.

The term "oxo" as used herein, alone or in combination, refers to a doubly bonded oxygen =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The term "phosphonate" as used herein, alone or in combination, refers to the —P(=O)(OG)(OG1) group, where G and G1 are chosen from H, alkyl, alkenyl, alkynyl, aryl, heteroaryl, etc.

The term "phosphinate" as used herein, alone or in combination, refers to the —P(=O)(G)(OG1) group, where G and G1 are chosen from H, alkyl, alkenyl, alkynyl, aryl, heteroaryl, etc.

The terms "sulfonate," "sulfonic acid," and "sulfonic," as used herein, alone or in combination, refers the —SO$_3$H group and its anion as the sulfonic acid is used in salt formation.

The term "sulfanyl," as used herein, alone or in combination, refers to —S and —S—.

The term "sulfinyl," as used herein, alone or in combination, refers to —S(O)—.

The term "sulfonyl," as used herein, alone or in combination, refers to —SO$_2$—.

The term "N-sulfonamido" refers to a RS(=O)$_2$NH— group with R as defined herein.

The term "S-sulfonamido" refers to a —S(=O)$_2$NR$_2$, group, with R as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

Prodrug Moiety

The compounds of the present embodiments are prodrugs of tizoxanide, an analogue or salt thereof, for example, analogues disclosed in U.S. Pat. Nos. 7,645,783, 7,550,493, 7,285,567, 6,117,894, 6,020,353, 5,968,961, 5,965,590, 5,935,591, and 5,886,013 and U.S. application Ser. Nos. 12/184,760, 12/656,704, 12/821,571, 12/777,383, 13/284,242, 13/471,948. In one embodiment, the tizoxanide, an analogue or salt thereof contains at least one hydroxy moiety on the phenyl ring. The corresponding prodrug contains an ester moiety comprising the amino acid moiety. In one embodiment, the tizoxanide analogue is identical to tizoxanide, except that the nitro group is replaced by Cl.

Amino acids used in the prodrugs of the present disclosure can by any natural or unnatural amino acid. For example, in one embodiment, the amino acid is selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. In one embodiment, the amino acid comprises a hydrophobic side chain, for example, alanine, isoleucine, leucine, methionine, phenylalanine, tryptophan, tyrosine, and valine. In one embodiment, the amino acid comprises an alkyl side chain, for example, alanine, isoleucine, leucine, and valine.

In another embodiment, the amino acid bound to tizoxanide, an analogue or salt thereof is represented by the following formula (A):

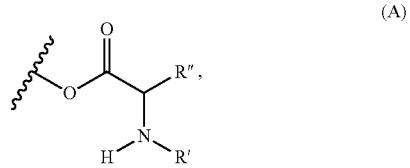

(A)

wherein R' is selected from the group consisting of hydrogen, alkyl, and a nitrogen protecting group;

R" is selected from the group consisting of alkyl, alkenyl, alkynyl, cycloalkyl, cycloalkylalkyl, cycloalkylalkenyl, cycloalkylalkynyl, cycloalkenyl, cycloalkenylalkyl, cycloalkenylalkenyl, cycloalkenylalkynyl.

In one embodiment, R' is selected from the group consisting of hydrogen and a nitrogen protecting group, and R" is a straight-chain, branched-chain, or cyclic unsaturated ($C_1$-$C_{10}$)-alkyl moiety. In another embodiment, R" is a straight-chain or branched-chain ($C_1$-$C_5$)-alkyl moiety or R" is a ($C_1$-$C_3$)-alkyl moiety or R" is a $C_3$-alkyl moiety. In some embodiments, R' is hydrogen.

The amino acid moiety may be racemic or may be optically active. In some embodiments, the amino acid moiety has an enantiomeric excess of at least 50, 60, 70, 80, 90, 95, 96, 97, 98, 99, 99.5, 99.9% or greater. IN one embodiment, wherein Formula A is a moiety selected from

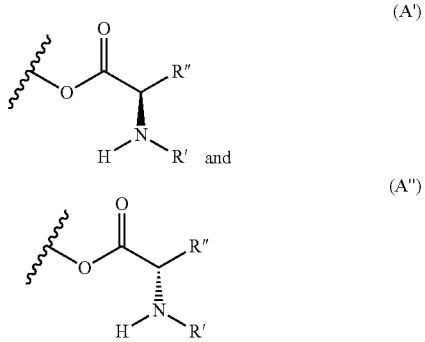

(A') and (A")

wherein R' and R" can be any of the previously defined values.

In other embodiments, the amino acid bound to tizoxanide, an analogue or salt thereof is represented by the following formula (A'):

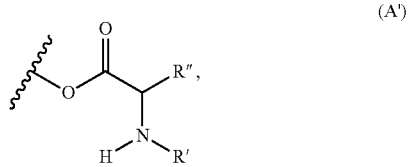

(A')

wherein R' is selected from the group consisting of hydrogen, alkyl, and a nitrogen protecting group;

R" is selected from the group consisting of alkyl, alkenyl, alkynyl, cycloalkyl, cycloalkylalkyl, cycloalkylalkenyl, cycloalkylalkynyl, cycloalkenyl, cycloalkenylalkyl, cycloalkenylalkenyl, cycloalkenylalkynyl, and wherein R" is substituted by one or more selected from the group of OH, $NH_2$, SeH, SH or $CONH_2$, or a protected OH, $NH_2$, SeH, SH or $CONH_2$.

In other embodiments, the amino acid bound to tizoxanide, an analogue or salt thereof is represented by the following formula (B):

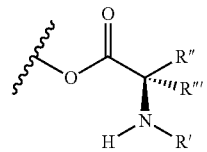

wherein R' is selected from the group consisting of hydrogen, alkyl, and a nitrogen protecting group;

R" and R'" are independently selected from the group consisting of alkyl, alkenyl, alkynyl, cycloalkyl, cycloalkylalkyl, cycloalkylalkenyl, cycloalkylalkynyl, cycloalkenyl, cycloalkenylalkyl, cycloalkenylalkenyl, cycloalkenylalkynyl, and wherein R" is optionally substituted by one or more selected from the group of OH, $NH_2$, SeH, SH or $CONH_2$, or a protected OH, $NH_2$, SeH, SH or $CONH_2$.

Protecting groups for OH, $NH_2$, ScH, SH or $CONH_2$ are known in the art, and are disclosed, for example, in Wuts, PGM Greene's Protective Groups in Organic Synthesis 4th edn (John Wiley & Sons, New York, 2007, which is incorporated by reference in its entirety.

Active Moiety

The active moiety of the present embodiments is prodrugs of tizoxanide or analogue or salts thereof. Examples of analogues within the scope of the disclosure are those listed in analogues disclosed in U.S. Pat. Nos. 7,645,783, 7,550, 493, 7,285,567, 6,117,894, 6,020,353, 5,968,961, 5,965,590, 5,935,591, and 5,886,013 and U.S. application Ser. Nos. 12/184,760, 12/656,704, 12/821,571, 12/777,383, 13/284, 242, 13/471,948. In one embodiment, the analogue is a compound of Formula (I)

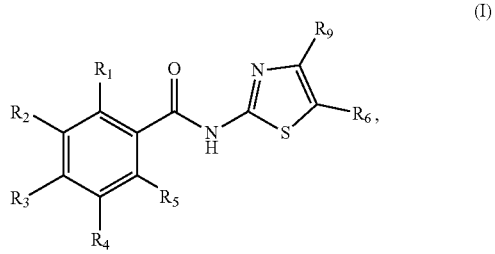

(I)

wherein $R_1$ through $R_5$ are, independently, selected from the group consisting of hydrogen, CN, $NO_2$, F, Cl, Br, I, hydroxy, alkyl, alkenyl, alkynyl, cycloalkyl, cycloalkylalkyl, cycloalkylalkenyl, cycloalkylalkynyl, cycloalkenyl, cycloalkenylalkyl, cycloalkenylalkenyl, cycloalkenylalkynyl, alkoxy, alkenyloxy, alkynyloxy, alkoxyalkyl, alkoxyalkenyl, alkoxyalkynyl, alkenyloxyalkyl, alkenyloxyalkenyl, alkenyloxyalkynyl, alkynyloxyalkyl, alkenyloxyalkenyl, alkenyloxyalkynyl, cycloalkoxy, cycloalkylalkoxy, cycloalkylalkenyloxy, cycloalkylalkynyloxy, cycloalkenyloxy, cycloalkenylalkoxy, cycloalkenylalkenyloxy, cycloalkenylalkynyloxy, alkoxyalkylamino, hydroxyalkyl, acyl, acyloxy, aroyloxy, arylalkanoyloxy, arylalkenoyloxy, heteroaroyloxy, heteroarylalkanoyloxy, heteroarylalkenoyloxy, alkoxycarbonyl, aryloxycarbonyl, arylalkoxycarbonyl, heteroaryloxycarbonyl, heteroarylalkoxycarbonyl, alkoxycarbonyloxy, carbamoyl, carbamoyloxy, alkylamino, dialkylamino, alkylaminoalkyl, amido, alkylamido, dialkylamido, haloalkyl, perhaloalkyl, perhaloalkoxy, alkylthio, alkylthioalkyl, alkylsulfonyl, alkylsulfonylalkyl, alkenylsulfonyl, alkynylsulfonyl, cycloalkylsulfonyl, cycloalkylalkylsulfonyl, cycloalkylsulfonylalkyl, cycloalkylalkylsulfonylalkyl, arylsulfonyl, arylalkylsulfonyl, arylalkenylsulfonyl, heteroarylsulfonyl, heteroarylalkylsulfonyl, heteroarylalkenylsulfonyl, alkylsulfonamido, N,N'-dialkylsulfonamido, sulfonamidoalkyl, sulfonamidoaryl, sulfonamidoarylalkyl, sulfonamidoarylalkenyl, aryl, arylalkyl, aryloxy, arylalkoxy, arylthio, arylalkylthio, arylamino, arylalkylamino, arylalkenyl, arylalkynyl, heteroaryl, heteroarylalkyl, heteroarylalkenyl, heteroarylalkynyl, heteroaryloxy, heteroarylalkoxy, heteroarylamino, heteroarylalkylamino, heteroarylthio, heteroarylalkylthio, heteroarylalkylamino, heterocycloalkyl, heterocycloalkenyl, heterocycloalkoxy, and heterocycloalkenyloxy, any of which may be optionally substituted, and where each of $R_1$ through $R_5$ comprises 1 to 60 atoms;

provided at least one of $R_1$ through $R_5$ is an amino acid moiety bound to the phenyl through an ester moiety, or a pharmaceutically acceptable salt thereof.

In one embodiment, $R_6$ is selected from the group consisting of $NO_2$, F, Cl, Br, —$SO_2$—($C_1$-$C_{10}$)-alkyl, —SO—($C_1$-$C_{10}$)-alkyl, haloalkyl, perhaloalkyl, haloalkoxy, perhaloalkoxy, $S(O)_mC(R_7R_8)_nCF_3$, and $C(R_7R_8)_nCF_3$, and $R_9$ is hydrogen, or wherein $R_9$ is selected from the group consisting of $NO_2$, F, Cl, Br, —$SO_2$—($C_1$-$C_{10}$)-alkyl, —SO—($C_1$-$C_{10}$)-alkyl, haloalkyl, perhaloalkyl, haloalkoxy, perhaloalkoxy, $S(O)_mC(R_7R_8)_nCF_3$, and $C(R_7R_8)_nCF_3$, and $R_6$ is hydrogen. In another embodiment, $R_6$ is selected from the group consisting of $NO_2$, F, Cl, Br, —$SO_2$—($C_1$-$C_{10}$)-alkyl, and —SO—($C_1$-$C_{10}$)-alkyl, and $R_9$ is hydrogen, or wherein $R_9$ is selected from the group consisting of $NO_2$, F, Cl, Br, —$SO_2$—($C_1$-$C_{10}$)-alkyl, and —SO—($C_1$-$C_{10}$)-alkyl, and $R_6$ is hydrogen. In yet another embodiment, R6 is selected from the group consisting of NO2 and Cl, and R9 is hydrogen, or wherein R9 is selected from the group consisting of NO2 and Cl, and R6 is hydrogen.

In a particular embodiment, $R_9$ is hydrogen. In another particular embodiment, $R_6$ is hydrogen.

In one embodiment, the compound is a compound of formula I, wherein one of $R_1$, $R_2$, and R3 is an amino acid moiety bound to the phenyl through an ester moiety $R_4$, $R_5$, and the remainder of $R_1$, $R_2$, and $R_3$, are H; and $R_6$ is $NO_2$ and $R_9$ is H.

In one embodiment, the compound is a compound of formula I, wherein $R_6$ is $NO_2$ and $R_9$ is H. In another embodiment, the compound is a compound of formula I, wherein $R_6$ is a halo, for example Cl or F and $R_9$ is H.

In one embodiment, the compound is selected from:

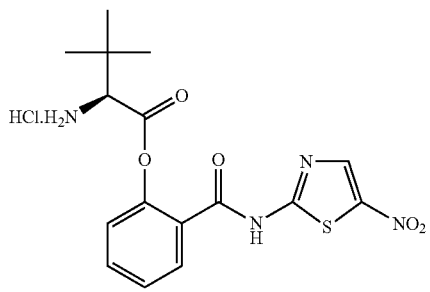

RM5061

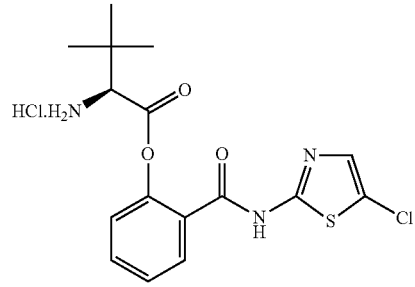

RM5064

1.RM5066

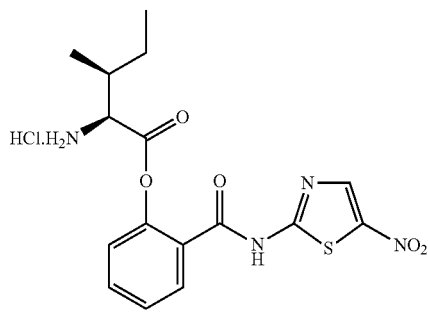

2.RM5065

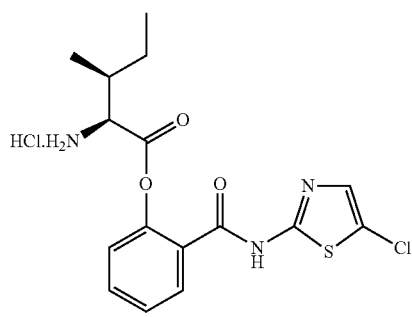

Other compounds listed in U.S. Pat. Nos. 7,645,783, 7,550,493, 7,285,567, 6,117,894, 6,020,353, 5,968,961, 5,965,590, 5,935,591, and 5,886,013 and U.S. application Ser. Nos. 12/184,760, 12/656,704, 12/821,571, 12/777,383, 13/284,242, 13/471,948 that contain at least one hydroxy moiety on a phenyl ring are incorporated in to this disclosure by reference and said compounds with an amino acid moiety bound to the phenyl through an ester moiety at the hydroxy moiety on the phenyl ring are compounds of this disclosure.

Pharmaceutical Compositions

The compounds of the present disclosure are capable of being incorporated into a pharmaceutical composition comprising the compound and at least one pharmaceutically acceptable excipient. In one embodiment, the pharmaceutical composition comprises a prodrug of tizoxanide or analogue of the present disclosure, or pharmaceutically acceptable salt thereof, and a pharmaceutically acceptable excipient. In one embodiment, the pharmaceutical composition is in the form of a solid oral dosage form, such as a tablet or capsule. In another embodiment, the pharmaceutical composition is in the form of a dosage form suitable for injection, such as intravenous administration.

The pharmaceutical composition may be in the form of an oral pharmaceutical that is immediate release or controlled release. The pharmaceutical composition may also comprise a compound of the present disclosure in addition to another pharmaceutical compound, e.g., nitazoxanide, tizoxanide or a compound listed in U.S. Pat. Nos. 7,645,783, 7,550,493, 7,285,567, 6,117,894, 6,020,353, 5,968,961, 5,965,590, 5,935,591, and 5,886,013 and U.S. application Ser. Nos. 12/184,760, 12/656,704, 12/821,571, 12/777,383, 13/284, 242, 13/471,948.

The pharmaceutical composition comprises an effective amount of a compound of the present disclosure. For example, in one embodiment, the pharmaceutical composition comprises 50 to 600 mg, or 300 to 600 mg or 50, 75, 100, 125, 150, 175, 200, 225, 250, 275, 300, 350, 400, 450, 500, 550, or 600 mg of a compound of the present disclosure. This weight is of the prodrug itself, or based on the weight of the active moiety.

The compositions can contain one or more additional pharmaceutically acceptable additives or excipients. In those embodiments with controlled release and immediate release portions, both the controlled release portion and the immediate release portion can contain one or more additional pharmaceutically acceptable additives or excipients. These excipients are therapeutically inert ingredients that are well known and appreciated in the art. As used herein, the term "inert ingredient" refers to those therapeutically inert ingredients that are well known in the art of pharmaceutical science, which can be used singly or in various combinations, and include, for example, diluents, disintegrants, binders, suspending agents, glidants, lubricants, fillers, coating agents, solubilizing agent, sweetening agents, coloring agents, flavoring agents, and antioxidants. See, for example, Remington: The Science and Practice of Pharmacy 1995, edited by E. W. Martin, Mack Publishing Company, 19th edition, Easton, Pa.

Examples diluents or fillers include, but are not limited to, starch, lactose, xylitol, sorbitol, confectioner's sugar, compressible sugar, dextrates, dextrin, dextrose, fructose, lactitol, mannitol, sucrose, talc, microcrystalline cellulose, calcium carbonate, calcium phosphate dibasic or tribasic, dicalcium phosphate dehydrate, calcium sulfate, and the like.

Diluent(s) or filler(s) typically represent about 2% to about 15% by weight of the entire composition.

Examples of disintegrants include, but are not limited to, alginic acid, methacrylic acid DVB, cross-linked PVP, microcrystalline cellulose, sodium croscarmellose, crospovidone, polacrilin potassium, sodium starch glycolate, starch, including corn or maize starch, pregelatinized starch and the like.

Disintegrant(s) typically represent about 2% to about 15% by weight of the entire composition.

Examples of binders include, but are not limited to, starches such as potato starch, wheat starch, corn starch; microcrystalline cellulose; celluloses such as hydroxypropyl cellulose, hydroxyethyl cellulose, hydroxypropylmethyl cellulose (HPMC), ethyl cellulose, sodium carboxy methyl cellulose; natural gums like acacia, alginic acid, guar gum; liquid glucose, dextrin, povidone, syrup, polyethylene oxide, polyvinyl pyrrolidone, poly-N-vinyl amide, polyethylene glycol, gelatin, poly propylene glycol, tragacanth, and the like.

Binder(s) typically represent about 0.2% to about 14% by weight of the entire composition.

Examples of glidants include, but are not limited to, silicon dioxide, colloidal anhydrous silica, magnesium trisilicate, tribasic calcium phosphate, calcium silicate, magnesium silicate, colloidal silicon dioxide, powdered cellulose, starch, talc, and the like.

Glidant(s) typically represent about 0.01% to about 0.3% by weight of the entire composition.

Examples of lubricants include, but are not limited to, magnesium stearate, aluminum stearate, calcium stearate, zinc stearate, stearic acid, polyethylene glycol, glyceryl behenate, mineral oil, sodium stearyl fumarate, talc, hydrogenated vegetable oil and the like.

Lubricant(s) typically represent about 0.2% to about 1.0% by weight of the entire composition.

The present compositions can further comprise a coating material. The coating material is typically present as an outer layer on the dosage form that completely covers the formulation. For example, in some embodiments, the dosage form is an oral tablet in which the controlled release portion forms a first layer of the tablet and the immediate release portion forms a second layer that is deposited on top of the first layer to form a core tablet. In such embodiments, e.g., the coating material can be in the form of an outer coating layer that is deposited on top of the core tablet.

The coating material typically is about 1% to about 5% by weight of the composition.

The coating material can comprise hydroxypropylmethylcellulose and/or polyethylene glycol, and can comprise one or more excipients selected from the group comprising coating agents, opacifiers, taste-masking agents, fillers, polishing agents, coloring agents, antitacking agents and the like. For example, the coating material can contain titanium dioxide as an opacifying agent. Examples of film-coating substances and methods for using such coating substances are well known to those of skill in the art.

In one embodiment, the coating is not an enteric coating. In another embodiment, the coating is an enteric coating.

For example, the coating material used in the present compositions can be OPADRY AMB 80W91416 or OPADRY FX 63F97546, as in the examples below.

The controlled release composition may deliver the compound via pH-dependent release, via microbially-triggered delivery, as a conjugate, via time-controlled delivery, via osmotically-regulated delivery, administered via pressure-controlled delivery, via multi matrix systems delivery, via bioadhesion delivery, or via multiparticulate delivery. The compound in the controlled release formulation may be released preferentially in the small or large intestine, colon or rectum, in the stomach, esophagus, for example. In some embodiments, at least 60%, 70%, 80%, or 90% of the administered dose of the compound is released in at least one of the recited regions of the body over a period of 2-24 hours, or 2, 3, 4, 5, 6, 7, 8, 9, 10, 11, 12, 13, 14, 15, 16, 17, 18, 19, 20, 21, 22, 23 or 24 hours.

Methods of making solid pharmaceutical formulations are known to those of skill in the art of pharmaceutical formulations and can be employed to prepare the present compositions. See, for example, Remington: The Science and Practice of Pharmacy (1995), edited by E. W. Martin, Mack Publishing Company, 19th edition, Easton, Pa.

One or more additional active agents may be included in the present pharmaceutical compositions and methods of treatment. For example, in some embodiments, the compositions may include one or more additional therapeutic agents useful in treating hepatitis C such as ribavirin, and immune-stimulating agents including, but not limited to, interferons such as interferon α-2b, a derivative of interferon α-2b such as a polyethylene glycol-conjugated form of interferon α-2b, interferon α-2a, or interferon alfacon-1.

Methods of Treatment

The present compositions can be used to effectively treat an intracellular bacterial infection, a viral infection or a cancer and provide increased bioavailability and better absorption of nitazoxanide, with fewer of the side effects commonly seen in standard nitazoxanide formulations. In some embodiments, the present compositions display a marked improvement in aqueous solubility, for example, the aqueous solubility of RM-5061 is 1 mg/mL ("very slightly soluble" to "slightly soluble") compared to <0.1 mg/ml ("practically insoluble") for nitazoxanide, thereby allowing for preparation of injectable, e.g., intravenous, formulations.

Treatment of intracellular bacterial infections with nitazoxanide is known in the art. The present methods provide for the treatment of a subject suffering from an intracellular bacterial infection comprising administering to the subject in need thereof a therapeutically effective amount of a compound or composition of the present disclosure. In one embodiment, the pharmaceutical composition is administered in an amount of 300 to 600 mg or 300, 350, 400, 450, 500, 550, or 600 mg of a compound of the present disclosure once a day or twice a day or three times a day. Treatment regimens may be adjusted based on the knowledge of one of ordinary skill. For example, the treatment regimen may be carried out over 1, 2, 3, 4, 5, 6, 7 days or 1, 2, 3, or 4 weeks. In one embodiment, the treatment of a subject suffering from an intracellular bacterial infection comprising administering to the subject in need thereof a therapeutically effective amount of a compound or composition of the present disclosure provides increased bioavailability or better absorption or with of the side effects than a comparative treatment with nitazoxanide.

In another particular aspect of the invention, the subject suffers from an intracellular protozoan infection. In a different particular aspect of the invention, the subject is at risk of developing an intracellular protozoan infection. In one embodiment, the intracellular protozoan infection is *Cryptosporidium* spp. In a different aspect of the invention, the intracellular protozoan infection is *Leishmania* spp. In yet another aspect of the invention, the intracellular protozoan infection is *Toxoplasma gondii*. In a further aspect of the invention, the intracellular protozoan infection is *Trypanosoma cruzii*. In one particular embodiment, the prodrug compound of the present disclosure is administered alone.

In another particular embodiment of the invention, the prodrug compound of the present disclosure is administered in combination with a vaccine, or an immunostimulant, or an antiprotozoal drug. The antiprotozoal drug may include, but is not limited to, trimethoprimisulfamethoxazole, atovaquone, clindamycin, pyrimethamine, spiramycin, diminazine, homidium, suramin, melarsamine, sodium stibogluconate and meglumine antimoniate.

Treatment of viral infections with nitazoxanide is known in the art. The present methods provide for the treatment of a subject suffering from a viral infection comprising administering to the subject in need thereof a therapeutically effective amount of a compound or composition of the present disclosure. In one embodiment, the pharmaceutical composition is administered in an amount of 300 to 600 mg or 300, 350, 400, 450, 500, 550, or 600 mg of a compound of the present disclosure once a day or twice a day or three times a day. Treatment regimens may be adjusted based on the knowledge of one of ordinary skill. For example, the treatment regimen may be carried out over 1, 2, 3, 4, 5, 6, 7 days or 1, 2, 3, or 4 weeks. In one embodiment, the treatment of a subject suffering from a viral infection comprising administering to the subject in need thereof a therapeutically effective amount of a compound or composition of the present disclosure provides increased bioavailability or better absorption or with of the side effects than a comparative treatment with nitazoxanide.

The viral infection may be a RNA virus or a DNA virus. RNA viruses of the present methods include: The Retroviridae: the Human Immunodeficiency Virus or HIV; the Reoviridae: the Norovirus or NoV; the Calciviridae: the rotavirus or RoV; the Flaviviridae: the Hepatitis C Virus or HCV; the Yellow Fever Virus or YFV; the Japanese Encephalitis Virus or JEV; the Dengue-2 Fever Virus or DEV; the orthomyxoviridae: the Influenza A Virus or IAV and the Influenza B Virus or IBV; the paramyxoviridae: the Parainfluenza Virus or HPIV and the Respiratory Scyncytial Virus or RSV; the coronaviridae: the Canine Coronavirus or CCoV and the Middle East Respiratory Virus or MERSCoV. In one embodiment, viral infection may be the MERS coronavirus in cell lines that express interferons.

DNA viruses of the present methods include: The Hepadnaviridae: the Hepatitis B Virus or HBV; the heipesviridae: the Herpes Simplex Virus-1 and -2 or HSV-1 and HSV-2; the Varicella Zoster.

In one embodiment, the treatment of the present disclosure is for HIV, HBV, HCV, NoV, RoV, YFV, JEV, DFV, IAV, IBV, HPIV, RSV, CCoV, MERSCoV, HSV-1, HSV-2, VZV.

The viral infection may be an influenza infection or may be caused by a virus selected from H1N1, H2N2, H3N2, H5N1, H7N7, H1N2, H9N2, H7N2, H7N3, and H10N7. In another embodiment, the treatment is of Influenza A virus including, H1N1-sensitive or oseltamivir resistant, H3N2-sensitive and oseltamivir or amantadine resistant, H3N2v, H3N8, H5N9, H7N9, H7N9-sensitive and oseltamivir resistant.

In another embodiment, the viral infection is Hepatitis B.

The treatment of a subject suffering from a viral infection or at risk of developing a viral infection comprising administering to the subject in need thereof a therapeutically effective amount of a compound or composition of the present disclosure may be in the form of mono-administration or co-administration. In one embodiment, the compound of composition is administered in combination with at least one additional component selected from the group consisting of a vaccine, neuraminidase inhibitor, such as Laninamivir, Oseltamivir, Zanamivir or Peramivir, or an immunostimulant, such as Imiquimod or Resiquimod, or an adamantine analogue, or a recombinant sialidase fusion protein, such as Fludase or an anti-hepatitis B drug.

In one embodiment, the treatment of a subject suffering from a viral infection comprising administering to the subject in need thereof a therapeutically effective amount of a compound or composition of the present disclosure provides increased bioavailability or better absorption or with of the side effects than a comparative treatment with nitazoxanide.

In another particular aspect of the invention, the subject suffers from a cancer. In a different particular aspect of the invention, the subject is at risk of developing a cancer. In one embodiment, the cancer is leukemia. Preferably, the leukemia is hairy cell leukemia or chronic myeloid leukemia. In a different aspect of the invention, the cancer is melanoma. In yet another aspect of the invention, the cancer is non-Hodgkin lymphoma. In a further aspect of the invention, the cancer is renal cell carcinoma. In a further aspect of the invention, the cancer is breast cancer or colon cancer or prostate cancer. In one particular embodiment, the prodrug compound of the present disclosure compound is administered alone. In another particular embodiment of the invention, the prodrug compound of the present disclosure is administered in combination with a vaccine, or an immunostimulant, or an anticancer drug. The anticancer drug may include, but is not limited to, STI571, CGP 74588, 1-β-D-Arabinofuranosylcytosine (Ara-C), doxorbicin, dacarbazine, cisplatin, bleomycin, vincristine, lomustine, vinblastine, carmustine, DTIC, tamoxifen, sunitinib, sorafenib and interferon-α. In one embodiment, the pharmaceutical composition is administered in an amount of 300 to 600 mg or 300, 350, 400, 450, 500, 550, or 600 mg of a compound of the present disclosure once a day or twice a day or three times a day. Treatment regimens may be adjusted based on the knowledge of one of ordinary skill. For example, the treatment regimen may be carried out over 1, 2, 3, 4, 5, 6, 7 days or 1, 2, 3, or 4 weeks.

In one embodiment, the treatment of a subject suffering from a cancer or at risk of developing a cancer comprising administering to the subject in need thereof a therapeutically effective amount of a compound or composition of the present disclosure provides increased bioavailability or better absorption or with of the side effects than a comparative treatment with nitazoxanide.

In one embodiment, the prodrug compound or composition of the present disclosure is administered to a subject in need thereof to stimulate an immune response. The prodrug compound or composition is administered in an immunostimulatory effective in amount. In one embodiment, the prodrug compound or composition of the present disclosure is administered with a vaccine to a subject in need thereof. The subject may be suffering from, or at risk of developing, a viral infection previously disclosed.

In one aspect, the prodrug compound of the present disclosure exhibits an increased bioavailability compared to an equivalent amount of the same nonprodrug compound. In some embodiments, the absolute bioavailability (measured by the area under the curve, AUC) upon administration of a prodrug compound of the present disclosure compared to the administration of an equivalent amount of the same nonprodrug compound is increased by about 5%, about 10%, about 15%, about 20%, about 25%, about 30%, about 35%, or about 40%.

In one aspect, the prodrug compound of the present disclosure exhibits a decreased amount of side effects compared to the equivalent amount of nitazoxanide. In some embodiments, the number of side effects observed upon administration of a prodrug compound of the present disclosure compared to the administration of an equivalent amount of nitazoxanide is increased by about 5%, about 10%, about 15%, about 20%, about 25%, about 30%, about 35%, or about 40%.

In one embodiment, the prodrug compound of the present disclosure is administered to a patent in need thereof without food.

In one embodiment, the composition of the present disclosure and the additional active agent (e.g., an interferon) may be administered simultaneously, or separately, at the same time, or in different compositions (including in separate compositions that vary in dosage form, release profiles, and the like).

It is to be understood that the description above as well as the examples that follow are intended to illustrate and not limit the scope of the invention. Other aspects, advantages and modifications within the scope of the invention will be apparent to those skilled in the art to which the invention pertains.

WORKING EXAMPLES

Example 1

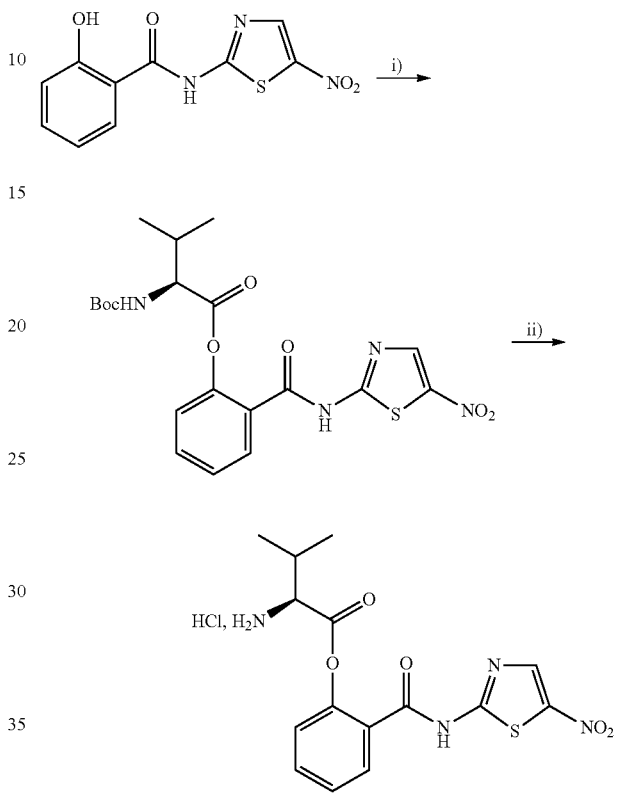

Scheme 1. Synthesis of a valinyl prodrug of tizoxanide.

Reagents: i) Boc-Val-OH, HATU, DMAP, THF;
ii) HCl-dioxan, 0-20° C.

Example 2

Synthesis of (S)-[2-[(5-nitro-1,3-thiazol-2-yl)carbamoyl]phenyl]-2-amino-3-methylbutanoate, hydrochloride Part 1: (S)-[2-[(5-nitro-1,3-thiazol-2-yl)carbamoyl]phenyl]-2-(t-butoxycarbonyl)amino-3-methylbutanoate: A mixture of t-butoxycarbonyl-L-valine (Boc-Val-OH; 0.21 g, 0.97 mmol) and tizoxanide (0.25 g, 0.94 mmol) was stirred at 20° C. in anhydrous THF (7.5 mL). HATU (viz. O-(7-Azabenzotriazole-1-yl)-1,1,3,3-tetramethyluronium hexafluorophosphate; 0.38 g, 1 mmol) was added in one portion, followed after 1 h by 4-dimethylaminopyridine (DMAP; 0.12 g, 1 mmol). After 20 h, the mixture was filtered through Celite and the precipitate washed with further THF then diluted with ethyl acetate (25 mL). The combined filtrate and washings were washed with 7% aq. citric acid, saturated aq. NaHCO$_3$, water and brine, then dried over anhydrous Na$_2$SO$_4$. Evaporation afforded a yellow foam which was chromatographed on silica gel, being applied in CH$_2$Cl$_2$ and eluted with 1:1 ethyl acetate: hexane. Appropriate fractions were combined and evaporated to afford the title compound as a white solid (280 mg); $^1$H NMR (400 MHz, CDCl$_3$) δ$_H$1.03, 1.12 (6H, 2d, Me$_2$CH), 1.40 (9H, s, Me₃CO), 2.35 (1H, m, Me₂CHCH), 4.39 (1H, m, CHCHNH), 5.20 (1H, m, NH), 7.40 (1H, d, ArH), 7.45 (1H, t, ArH), 7.67 (1H, t, ArH), 8.06 (1H, d, ArH), 8.18 (1H, s, thiazole 4-H) and 11.10 (1H, br s, NH); m/z (Electrospray +ve mode) 487 (MNa$^+$, base peak). Found: m/z, 487.1265. $C_{20}H_{24}N_4O_7S$ requires m/z, 487.1263.

Part 2: (S)-[2-[(5-nitro-1,3-thiazol-2-yl)carbamoyl]phenyl]-2-amino-3-methylbutanoate, hydrochloride: The preceding Boc derivative (0.250 g, 0.54 mmol) dissolved in $CH_2Cl_2$ (5 mL) was treated with 4M HCl in dioxan (2.5 mL) and stirred at 20° C. for 20 h. Much solid had already precipitated, and after adding diethyl ether (Et₂O, 10 mL) and stirring for a further 0.5 h, the precipitate was filtered off, washed with Et₂O and dried in vacuo to afford the title compound (0.220 g) as a very light yellow solid; ¹H NMR [400 MHz, (CD₃)SO] $δ_H$1.05 (6H, 2d, Me₂CH), 2.37 (1H, m, Me₂CHCH), 4.17 (1H, m, CHCHNH), 7.49 (1H, d, ArH), 7.53 (1H, t, ArH), 7.76 (1H, t, ArH), 7.90 (1H, d, ArH), 8.74 (1H, s, thiazole 4-H), 8.80-8.90 (3H, br s, H₃N$^+$) and 13.80 (1H, br s, NH; m/z (Electrospray +ve mode) 387 (MNa$^+$ of the free amine, base peak). Found: m/z, 387.0722. $C_{15}H_{16}N_4O_5SNa$ requires m/z, 387.0739.

Scheme 2. Synthesis of a tert-leucinylprodrug of tizoxanide.

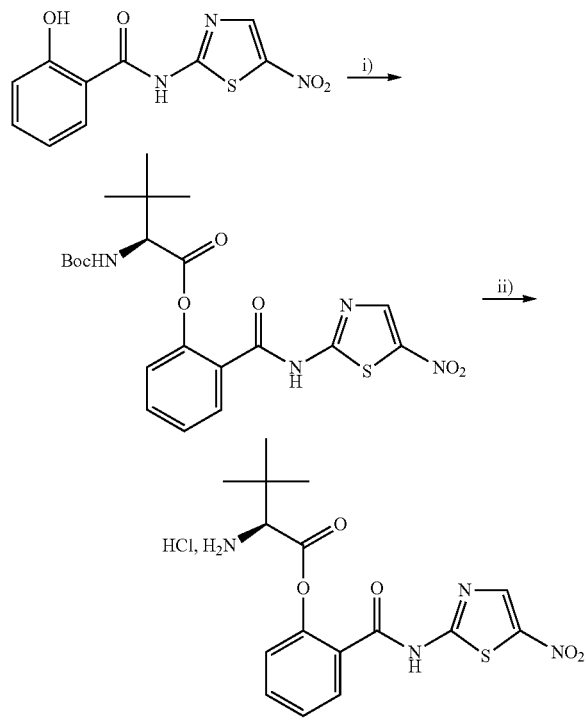

Reagents: i) Boc-Tle-OH, EDC, DMAP, THF;
ii) HCl-dioxan, 0-20° C.

Example 3

Synthesis of (S)-[2-[(5-nitro-1,3-thiazol-2-yl)carbamoyl]phenyl]-2-amino-3,3-dimethylbutanoate, hydrochloride Part 1: (S)-[2-[(5-nitro-1,3-thiazol-2-yl)carbamoyl]phenyl]-2-(t-butoxycarbonyl)amino-3,3-dimethylbutanoate: A mixture of t-butoxycarbonyl-L-tert-leucine (Boc-Tle-OH, 0.23 g, 1 mmol) and tizoxanide (0.26 g, 1 mmol) was stirred at 20° C. in a mixture of anhydrous THF (10 mL) and anhydrous DMF (4 mL), then treated with N-ethyl-N'-3-(dimethylamino)propyl carbodiimide.HCl (EDC; 0.19 g, 1 mmol) and DMAP (0.12 g, 1 mmol). After 26 h the mixture was worked up as described in Example 1 to give crude product as a yellow foam (0.260 g); ¹H NMR (400 MHz, CDCl₃) $δ_H$1.15 (9H, s, Me₃CC), 1.38 (9H, s, Me₃CO), 4.25 (1H, d, CHNH), 5.22 (1H, br d, CHNH), 7.40-7.50 (2H, m, ArH), 7.67 (1H, t, ArH), 8.09 (1H, d, ArH), 8.26 (1H, s, thiazole 4-H) and 11.10 (1H, br s, NH); m/z (Electrospray +ve mode) 501 (MNa$^+$, base peak). Found: m/z, 501.1417. $C_{21}H_{26}N_4O_7SNa$ requires m/z, 501.1420.

Part 2: (S)-[2-[(5-nitro-1,3-thiazol-2-yl)carbamoyl]phenyl]-2-amino-3,3-dimethylbutanoate, hydrochloride: The preceding Boc derivative (0.254 g, 0.53 mmol) was suspended in $CH_2Cl_2$ (5 mL) and 4M HCl in dioxan (2 mL) was added with stirring at 20° C. A solution resulted after a few minutes, but solid soon began to precipitate. After 16 h, the reaction was worked up as described for Example 1 to afford the title compound (0.205 g); ¹H NMR [400 MHz, (CD₃)SO] $δ_H$ 1.10 (9H, s, Me₃C), 4.00 (1H, s, CHNH₃$^+$), 7.54 (1H, d, ArH), 7.62 (1H, t, ArH), 7.75 (1H, t, ArH), 7.85 (1H, d, ArH), 8.73 (1H, s, thiazole 4-H), 8.86 (3H, br s, NH₃) and 13.85 (1H, br s, NH); ¹³C NMR [100 MHz, (CD₃)SO] $δ_C$ 26.6, 33.9, 61.5, 124.0, 126.6, 127.1, 130.0, 133.7, 142.6, 143.0, 147.8, 162.2, 165.8 and 167.5; m/z (Electrospray +ve mode) 379 (base peak, ammonium ion). Found: m/z, 379.1060. $C_{16}H_{19}N_4O_5S$ requires m/z, 379.1076.

Example 4

Two groups of three male Sprague-Dawley rats were administered RM-5061 as a single oral or bolus intravenous dose as detailed in the table below:

| Group # | # of Animals and Sex | Route of Administration | Targeted Dose Conc. (mg/mL) | Targeted Dose Vol. (mL/kg) | Targeted Dose Level (mg/kg) |
|---|---|---|---|---|---|
| 1 | 3M | PO | 6 | 5 | 30 |
| 2 | 3M | IV | 5.42 | 1.11 | 6 |

Serial blood samples were obtained from each animal at 0.083, 0.167, 0.25, 0.5, 1, 2, 4, 8, 12, and 24 hours post-dose. Pharmacokinetic parameters for tizoxanide and tizoxanide glucuronide following a single oral or a single intravenous dose of RM-5061 are summarized in the table below.

| Route | RM-5061 dose (mg/kg) | Analyte | $C_{max}$ (μg/mL) | $T_{max}$ (hr) | $AUC_{last}$ (μg*hr/mL) | $AUC_{0-inf}$ (μg*hr/mL) | $T_{1/2,e}$ (hr) | F |
|---|---|---|---|---|---|---|---|---|
| PO | 28.0 ± 0.75 (2.7) | Tizoxanide | 6.19 ± 0.786 (12.7) | 0.167 ± 0.0835 (50.1) | 3.12 ± 0.347 (11.1) | 3.17 ± 0.333 (10.5) | 0.554 ± 0.3634 (65.6) | 0.13 ± 0.0150 (11.1) |
| | | Tizox. glucuronide | 18.6 ± 2.83 (15.2) | 0.5 ± 0.00 (0.0) | 21.4 ± 4.71 (22.0) | 23.6 ± 4.52 (19.2) | 1.01 ± 0.45 (44.8) | |

-continued

| Route | RM-5061 dose (mg/kg) | Analyte | $C_{max}$ (μg/mL) | $T_{max}$ (hr) | $AUC_{last}$ (μg*hr/mL) | $AUC_{0\text{-}inf}$ (μg*hr/mL) | $T_{1/2,e}$ (hr) | F |
|---|---|---|---|---|---|---|---|---|
| IV | 6.30 ± 0.145 (2.3) | Tizoxanide | 12.8 ± 4.33 (33.9) | 0.083 ± 0.000 (0.0) | 5.21 ± 2.757 (52.9) | 6.31 ± 4.585 (72.7) | 0.381 ± 0.1341 (35.2) | |
| | | Tizox. glucuronide | 7.89 ± 1.824 (23.1) | 0.75 ± 0.433 (57.7) | 13.4 ± 10.40 (77.6) | 17.6[a] | 1.27[a] | |

Mean ± SD (% RSD); N = 3
[a]Mean of two.

Following oral dose administration of RM-5061 at ~28 mg/kg, tizoxanide was detected in the plasma as early as the first blood sampling timepoint of 0.083 hours in all three animals. The greatest plasma concentration of tizoxanide following oral administration of RM-5061 occurred between 0.083 and 0.25 hours post-oral dose. The last quantifiable tizoxanide plasma concentration for the three animals occurred at 2 and 4 hours post-oral dose. Mean tizoxanide plasma elimination half-life was 0.55 hours. Tizoxanide was quickly metabolized to its glucuronide. Tizoxanide glucuronide was detected in plasma in the first blood sampling timepoint of 0.083 hours. Maximum tizoxanide glucuronide plasma concentrations were observed at 0.5 hours post-oral dose. Tizoxanide glucuronide Cmax values were approximately 3-4 times greater than tizoxanide Cmax values. Tizoxanide glucuronide AUC values were –5-8 times greater than tizoxanide AUC values which suggested rapid glucuronidation. Mean tizoxanide glucuronide $T_{1/2,e}$ was 1.01 hours. An estimate of the oral bioavailability of tizoxanide was low, ~13%, which was more consistent with its rapid metabolism to tizoxanide glucuronide than the extent of absorption of the prodrug RM-5061 and its conversion to tizoxanide.

Following intravenous dose administration of RM-5061 at ~6.3 mg/kg, tizoxanide was detected in the plasma at the first blood sampling timepoint of 0.083 hours. The greatest plasma concentration of tizoxanide following intravenous administration of RM-5061 occurred at the first blood sampling timepoint of 0.083 hours. The last quantifiable tizoxanide plasma concentration for the three animals occurred at 1 and 2 hours post-intravenous dose. Mean tizoxanide plasma elimination half-life was 0.38 hours. Tizoxanide was quickly metabolized to its glucuronide. Tizoxanide glucuronide was detected in plasma in the first blood sampling timepoint of 0.083 hours. Maximum tizoxanide glucuronide plasma concentrations were observed at 0.25 and 1 hour post-intravenous dose.

Tizoxanide glucuronide Cmax values were slightly less than tizoxanide Cmax values. Tizoxanide glucuronide AUC values were –2 to 7 times greater than tizoxanide AUC values in two of three animals. Individual tizoxanide glucuronide $T_{1/2,e}$ values were 0.55 and 2 hours; in Rat 1287, the terminal elimination phase in plasma was not observed since it was found dead at 2 hours post-intravenous dose. One should note that the tizoxanide plasma concentrations of Rat 1287 were greater than those concentrations of the other two animals over the 0.083 to 1 hour timeframe.

Compared to a similar study for Nitazoxanide, where the respective drugs were administered orally by gavage at a dose of ~30 mg/kg to rats, and the oral formulation of each drug was prepared at a concentration of 6 mg of drug/ml of vehicle (0.5% carboxymethylcellulose in water), and where the nitazoxanide study used 3 male rats and 3 females while the RM-5061 study used 3 male rats, and comparing pharmacokinetics parameters for males to males, the mean maximum plasma concentrations (Cmax) of the tizoxanide metabolite were 6.19+0.786 μg/ml following oral administration of RM-5061 compared to only 0.454+0.0895 μg/ml following oral administration of nitazoxanide (a 13.6-fold increase). The mean Cmax of the tizoxanide glucuronide metabolite were 18.6+2.83 μg/ml following oral administration of RM-5061 compared to only 3.49+1.089 μg/ml following oral administration of nitazoxanide (a 5.33-fold increase). Importantly, the % Relative Standard Deviation (% RSD) for the Cmax values were lower following oral administration of RM-5061 (12.7% for tizoxanide Cmax and 15.2% for tizoxanide glucuronide Cmax) compared to those following oral administration of nitazoxanide (19.7% for tizoxanide Cmax and 31.2% for tizoxanide glucuronide Cmax). These data indicate that RM-5061 administered orally delivers much higher concentrations of tizoxanide and tizoxanide glucuronide, and the absorption is associated with less variability. One of the problems associated with nitazoxanide in humans is that its absorption is highly variable and that it must be administered with food to improve absorption (approximately doubled with food). This data suggests that RM-5061 will deliver higher plasma concentrations of tizoxanide (the active metabolite) with less variability and perhaps without requiring co-administration with food.

Example 5

Patents are administered the compound of Example 1 orally at 300, 400 or 500 mg twice per day for one week. A control group is administered an equivalent amount if nitazoxanide orally at 300, 400 or 500 mg twice per day for one week. Plasma levels of active tizoxanide are monitored in all patient populations during the administration. The bioavailability of the administered agent increases in the patient population receiving the compound of Example 1 in relation to the patient population receiving nitazoxanide.

What is claimed is:
1. A compound having formula:

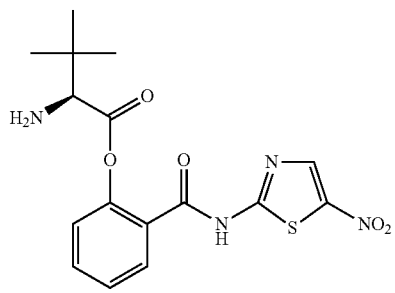 [SMILES: CC(C)(C)[C@H](N)C(=O)Oc1ccccc1C(=O)Nc1ncc([N+](=O)[O-])s1]

or a pharmaceutically acceptable salt thereof.

2. A pharmaceutically acceptable salt of the compound of claim 1.

3. The salt of claim 2, which is a hydrochloric salt.

4. A pharmaceutical composition comprising the compound of claim 1 or its pharmaceutically acceptable salt.

5. The pharmaceutical composition of claim 4, wherein the composition is an injectable formulation.

6. The pharmaceutical composition of claim 4, wherein the composition is an intravenous formulation.

7. The pharmaceutical composition of claim 5, comprising an aqueous solution of the compound or its pharmaceutically acceptable salt.

8. The pharmaceutical composition of claim 4 in a dosage form suitable for injection.

9. The pharmaceutical composition of claim 8, wherein the dosage form is suitable for intravenous administration.

10. The pharmaceutical composition of claim 4, wherein the composition is an oral formulation.

11. A pharmaceutical formulation comprising an aqueous solution of the compound of claim 1 or its pharmaceutically acceptable salt.

* * * * *